United States Patent [19]
Steen

[11] Patent Number: 5,935,595
[45] Date of Patent: Aug. 10, 1999

[54] DEVICE AND METHOD FOR REDUCING WOUND TRAUMA

[76] Inventor: Mary Steen, 27 Bryony Street, Leeds, LS10 4SS, United Kingdom

[21] Appl. No.: 08/854,248

[22] Filed: May 8, 1997

[51] Int. Cl.$^6$ ................................................ A61F 13/00
[52] U.S. Cl. ........................... 424/443; 602/41; 602/67; 604/304
[58] Field of Search ............................ 424/443; 602/41, 602/67; 604/304

[56] References Cited

U.S. PATENT DOCUMENTS

| | | | |
|---|---|---|---|
| 3,175,558 | 3/1965 | Caillouette | 128/403 |
| 3,780,537 | 12/1973 | Spencer | 62/530 |
| 3,809,096 | 5/1974 | York | 128/403 |
| 3,885,403 | 5/1975 | Spencer | 62/530 |
| 3,929,131 | 12/1975 | Hardwick | 128/254 |
| 3,939,842 | 2/1976 | Harris | 128/401 |
| 4,240,436 | 12/1980 | Singleton | 128/403 |
| 4,844,073 | 7/1989 | Pohler | 128/401 |
| 5,062,425 | 11/1991 | Tucker | 128/401 |
| 5,167,655 | 12/1992 | McCoy | 604/396 |
| 5,476,491 | 12/1995 | Mayn | 607/111 |

FOREIGN PATENT DOCUMENTS

| | | |
|---|---|---|
| 0 162 583 A2 | 11/1985 | European Pat. Off. . |
| 0 449 299 A1 | 10/1991 | European Pat. Off. . |
| 2 169 425 | 12/1985 | United Kingdom . |
| 2 261 438 | 5/1993 | United Kingdom . |

*Primary Examiner*—D. Gabrielle Brouillette
*Attorney, Agent, or Firm*—Rohm & Monsanto, P.L.C.

[57] ABSTRACT

The device according to this invention is provided to reduce the trauma which can be caused by an open wound such as that caused after childbirth and in particular to reduce the trauma of an open wound in the perineal and/or rectal area which can be painful and uncomfortable to a person having experienced childbirth. The device comprises a housing having a gel-like material therein which can be cooled prior to application to the area and said material has a high thermal capacity so that when the device is applied a cooling effect is created, an occluding effect of the open wound is provided and furthermore a cushioning effect on the area surrounding the wound is also provided thereby allowing the device to be used comfortably and also to improve the comfort of the person to whom the same is applied.

25 Claims, 5 Drawing Sheets

DEVICE AND METHOD FOR REDUCING WOUND TRAUMA

The invention which is the subject of this application is a device to alleviate the condition of pain and trauma caused by open wounds in persons and particularly for use in relation to perineal and rectal trauma and to which reference is made herein in but which should not be read as a restriction on the possible scope of the use of the device.

Perineal and rectal trauma can cause a great deal of distress and discomfort in many women before and following childbirth which may last for a considerable period of time thereafter. It is found that perineal trauma is especially prevalent amongst women who have experienced childbirth with the use of forceps and other instruments. It is now known and accepted that this can cause considerable distress and suffering to these women. It is also known that many women experience problems with haemorrhoids before and after delivery.

The short term effects of perineal and rectal trauma can inhibit a woman from mobilising fully, prevent her from sitting down comfortably and impair her ability or willingness to care for her newborn baby. It is also known that perineal trauma can increase the problems of insomnia, reduce appetite, interfere with lactation and, in conjunction with depression, which is sometimes encountered, can lead to maternal exhaustion. A long term effect can be the occurrence of dyspareunia.

Perineal trauma occurs in approximately 70% of women following childbirth. It is accompanied by a wound which is open and typically stitched up and this, therefore, provides further consideration to be taken into account when suggesting treatment for the same.

It is conventionally known that perineal/rectal trauma is a problem but there is no specific device available which is directed towards alleviating this peculiar and most traumatic condition. A common approach is to provide an ice pack which when applied to the painful area appears to have the effect of numbing the soft tissue which does give some temporary relief. However, problems associated with this type of ice pack are that it is hard, inflexible, uncomfortable to wear and in addition, the ice melts relatively quickly, therefore, any relief from the pain is relatively short. The ice pack was not specifically designed to treat this condition and is simply a frozen salt water sachet normally used for other purposes, e.g., irritated wounds and is too small to occlude the perineal/rectal area. This ice pack does not relieve pressure on the perineum when the woman is seated. It also causes increased work load to the persons looking after the woman or indeed, the woman herself when discharged from hospital as she will have to remove and replace ice packs at regular intervals to maintain relief from the pain. Furthermore, it has been suggested that this relief, which is due to the numbing effect, has the accompanying problem of vaso-constriction which may delay the healing process of the wound. This is unsatisfactory as the underlying aim is to allow the wound to heal as quickly as possible. This use of ice packs is, however, the most commonly used localised treatment for relieving perineal pain.

It is also known to use large gel-packs as a compress which can be heated or cooled but these are bulky and are provided for use on bumps such as, on legs or arms, and are marketed for sports injuries but not for use in relation to areas having open wounds. These are not provided in a form which is suitable for use to relieve perineal/rectal trauma and not designed to alleviate perineal/rectal pressure.

An alternative conventional approach is to use a substance known under the trade name Epifoam which is an anti-inflammatory steroid agent devised for the treatment of perineal pain. It's physical appearance is a white foam which is applied directly to the wound, therefore, it does not give either a cooling or pressure-relieving effect. It is also relatively expensive. In addition, there is evidence to suggest that the use of this agent can cause the open wound structure to break down and hence, while it may relieve pain, Epifoam may cause damage to the wound itself.

It is therefore clear that there is a need for a satisfactory and effective device to be used by women to relieve perineal/rectal trauma caused by childbirth which is also designed to alleviate pressure on the damaged perineum and which does not unduly affect the open wound.

The idea of this invention is to provide a device containing an effective agent, which is specifically designed for the relief of perineal trauma by cooling and occluding the area. Shaped and mouldable as the gel is fluid even below freezing, to the particular shape to give optimum relief, it is also provided in a manner to allow the same to be applied in the required position as a cushion to alleviate pressure on the perineum. In addition, it has the benefit of repeated usage, and therefore is a valuable cost-effective invention.

In a first aspect of the invention there is provided a device for use for the relief of perineal and/or rectal trauma, said device comprising a housing within which is sealed a gel or fluid material which has a relatively high thermal capacity and, wherein said device is provided for direct application to the perineal and/or rectal area to provide a cooling effect on the affected area, and/or an occluding effect on an open wound and/or a cushioning effect on the affected area and any combination thereof.

Typically the housing is formed of flexible material and, held in a sealed condition within the housing is a fluid or gel material which even when cooled retains its fluid, pliable state or gel-like consistency at 0 degrees Celsius and preferably at −10 degrees celsius.

This invention provides a device to inhibit the inflammatory response of a traumatised area without delaying normal healing leading to the reduction in the swelling of the area and a decrease in soreness and pain.

It is envisaged that the gel used is a non-toxic gel which is preferably water soluble and has the characteristic of having a high thermal capacity which means that it is possible to cool the device by placing the same in a freezer but the gel material does not freeze and the device remains pliable. Furthermore, the material retains its cold condition for a relatively long period of time, thereby increasing the effectiveness of the pad when applied to the perineal/rectal area and so reducing the frequency with which the device is required to be replaced.

Typically the gel includes a gelling agent, an anti-freezing agent and optionally, but preferably, an antibiotic and colourant with the remainder being made up of a liquid such as water. A preferred gel composition and materials are: 5–7% hydroxy ethyl cellulose (gelling agent), 30–40% propylene glycol (anti-freezing agent) up to 0.2% sodium Nipsept (antibiotic) and up to 0.001% (colourant). Tests have indicated that a particularly appropriate composition is 5–6% hydroxy ethyl cellulose, 35% propylene glycol, 0.12% sodium Nipsept, 0.001% colourant with the remainder made up of water.

In a preferred embodiment, the device is provided in a relatively long elongate form for use in the perineal rectal area, approximately 20–25 cm long, 1–2 cm thick and between 3–4 cm in width. This shape is designed to cover the damaged perineal/rectal area and can be used in conjunction with a maternity pad following childbirth.

Typically the housing is formed with two layers of flexible material such as plastic sheet material, sealed or joined along their edges such that the gel-like material is held in a sealed container within the housing.

In a preferred embodiment, the pad is provided in a flexible form such that it can be used in conjunction with a sanitary towel. In a yet further embodiment, the device may be provided with adhesive wing portions which allow the device to be attached to the surrounding area and/or an undergarment thereby maintaining the device in the required position.

In a further feature of the invention there is provided a device for application to the perineal/rectal area to relieve trauma, said device having a first layer and a second layer, said layers sealed along their respective common edges to form a housing within which is provided a gel and said device is formed with an elongate body for application along the perineal area.

In a further aspect of the invention there is provided a device comprising a housing in which is sealed a gel or liquid material which has high thermal capacity characteristics when cooled to at least 0 degrees Celsius and wherein said device is applied to an open wound on a person to provide a cooling and occluding effect on said open wound and surrounding area.

In one embodiment the device also has a cushioning effect if used on a part of the body where pressure is applied.

In a yet further aspect of the invention there is provided a method of treating a person for the relief of perineal and/or rectal trauma, by application of a device to an affected area, said device comprising a housing, said housing containing a gel or fluid material, said gel being sealed within said housing and said gel being of high thermal capacity, wherein said device is cooled and directly applied to the perineal and/or rectal area to provide a cooling effect on the affected area, and/or an occluding effect on the open wound and/or a cushioning effect on the affected area and any combination thereof.

The invention also provides for the method of treating a person with an open wound by application of a device onto the open wound, said device comprising a housing in which is sealed a gel or liquid material which has high thermal capacity so as to have non-freezing characteristics at 0 degrees Celsius and wherein said device is applied to an open wound on a person to provide a cooling and occluding effect on said open wound.

BRIEF DESCRIPTION OF THE DRAWINGS

Specific embodiments of the invention are now described with reference to the accompanying drawings, wherein:

Referring now to FIG. 1, there is illustrated a device 2 according to the invention which in this case is shaped for use for the relief of perineal pain and/or trauma. The device includes first and second layers 4 and 6 which are sealed around the respective edges 8 to form a housing in which there is provided a gel or liquid material or substance. The device in the embodiment shown is provided in a relatively long, thin form to allow the same to be comfortably applied to the perineal/rectal area for which it is specifically designed.

FIG. 2 illustrates a preferred embodiment wherein the device is provided in a form where there is again provided first and second layers 14 and 16 which are sealed around the respective edges 18 to form a housing 20 in which there is provided a gel or liquid substance 22. Intermediate the elongate edges of the device there are provided wing portions 24, 26. Typically the wing portions can be provided with a layer of adhesive to allow the same to be applied to the area of the body surrounding the wound or affected area and/or under garment to allow the device to be retained in the required position to maintain the relief from perineal/rectal trauma.

FIG. 3 illustrates a cross section of FIG. 2 along line A—A and clearly shows the gel or liquid substance 22 held between the two layers 14 and 16 which are sealed along their common edges 18. Depending outwardly from said edges 18 are the winged portions 24, 26 with the layers of adhesive 29 thereon.

To use the device the same is first placed in a freezer or other cooling means, typically for two hours to reduce the temperature of the gel to approximately −10 C. as shown in FIG. 4. Once the same has been placed in the cooling means for a sufficient period of time for the device to be sufficiently cool, the same can then be removed and is still maintained in its flexible condition. The device is preferably covered by a gauze sleeve and then placed on the perineal/rectal area to provide a cooling, occluding and cushioning effect which is known to reduce the trauma and discomfort experienced. As the substance 22 has a high thermal capacity and therefore maintains the relatively cool temperature conditions for an extended period of time, up to 30 minutes in tests, See FIG. 5, so the device can be used to reduce trauma and discomfort for a much greater period than is possible with conventional ice packs. Furthermore, direct contact of the substance in the housing with the wound is prevented, hence the numbing effect and risk of delay in wound healing, which can be a problem with conventional techniques is avoided.

Typically the device is shaped so as to render the same convenient to apply and it is envisaged that there are distinct advantages of using a device according to this invention, namely the device is safe to use with open wounds, and the duration of relief from pain is significantly extended over a considerable length of time. Furthermore the device can be applied and used by the person suffering from the pain without the need for medical assistance. The provision of the device with attachment means further enhances the utility of the device which will ensure that the device is kept in the required position.

Another feature is that the device can be used for the relief of pain and/or irritation caused by infection or surgery of the perineal/rectal area by applying the pad to act in a non-wetting manner over the area of irritation or inflammation.

Typically the material used for the pad is hygienic and acceptable for medical purposes.

Figure 1:
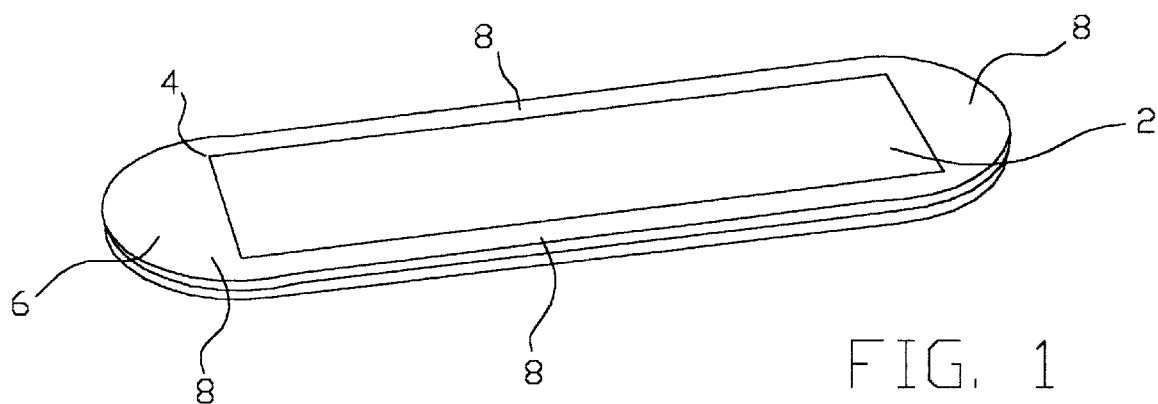
FIG. 1. illustrates one form of the device of the invention.
Figure 2:
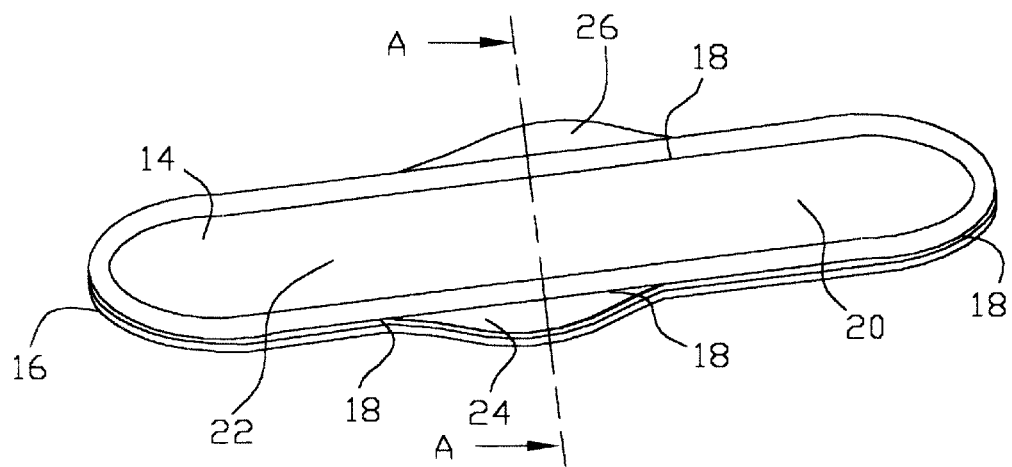
FIG. 2. illustrates a second preferred form of a device according to the invention.
Figure 3:
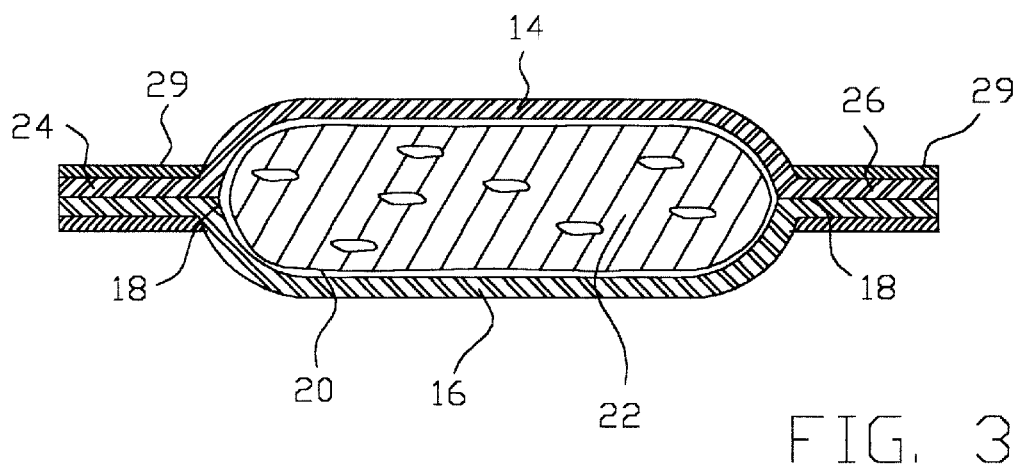
FIG. 3. illustrates a cross section through the device of FIG. 2. along line A—A.
Figure 4:
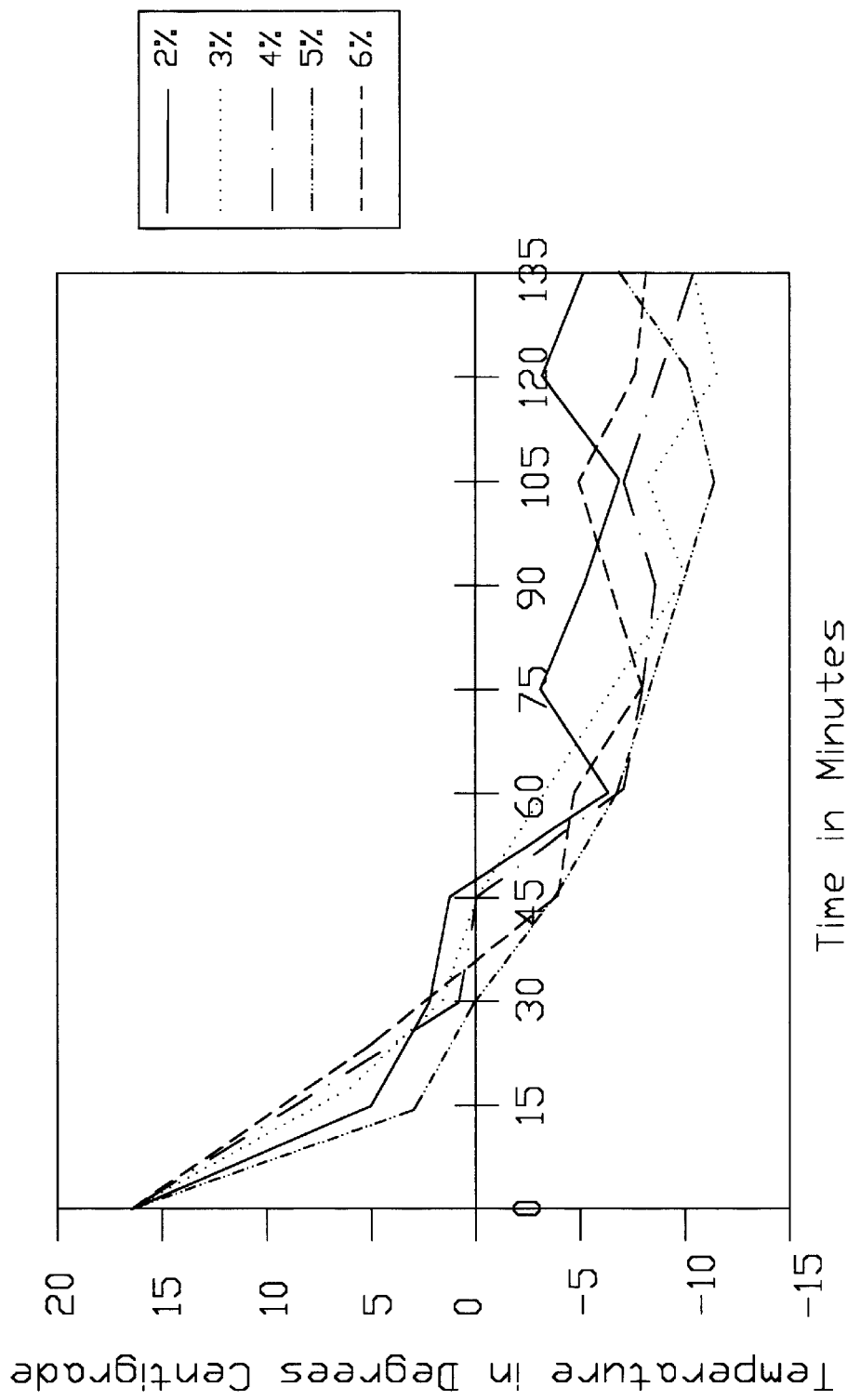
FIGS. 4–7 illustrate results obtained from tests using the device according to the invention in comparison with conventional techniques.
Figure 5:
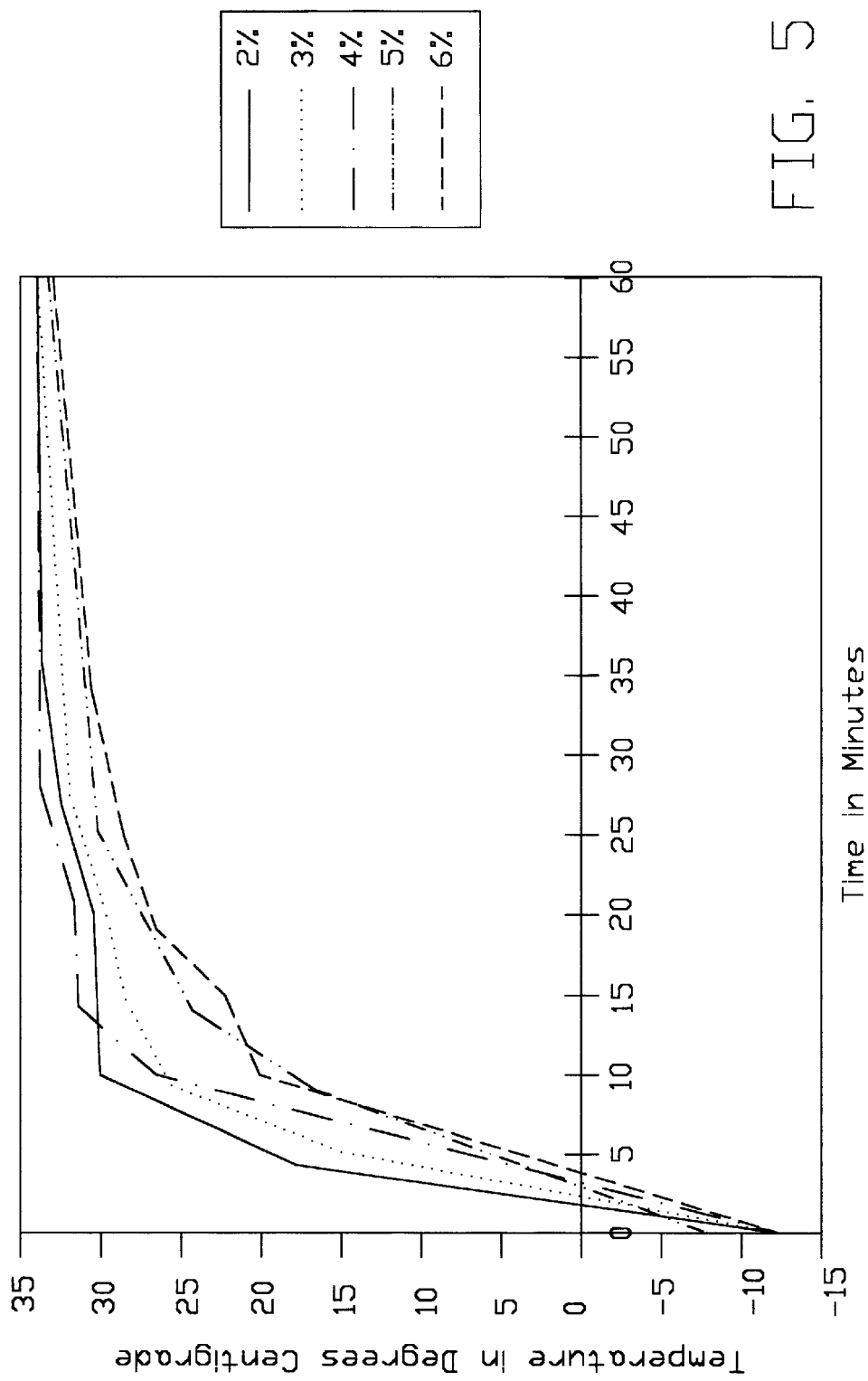
Figure 6:
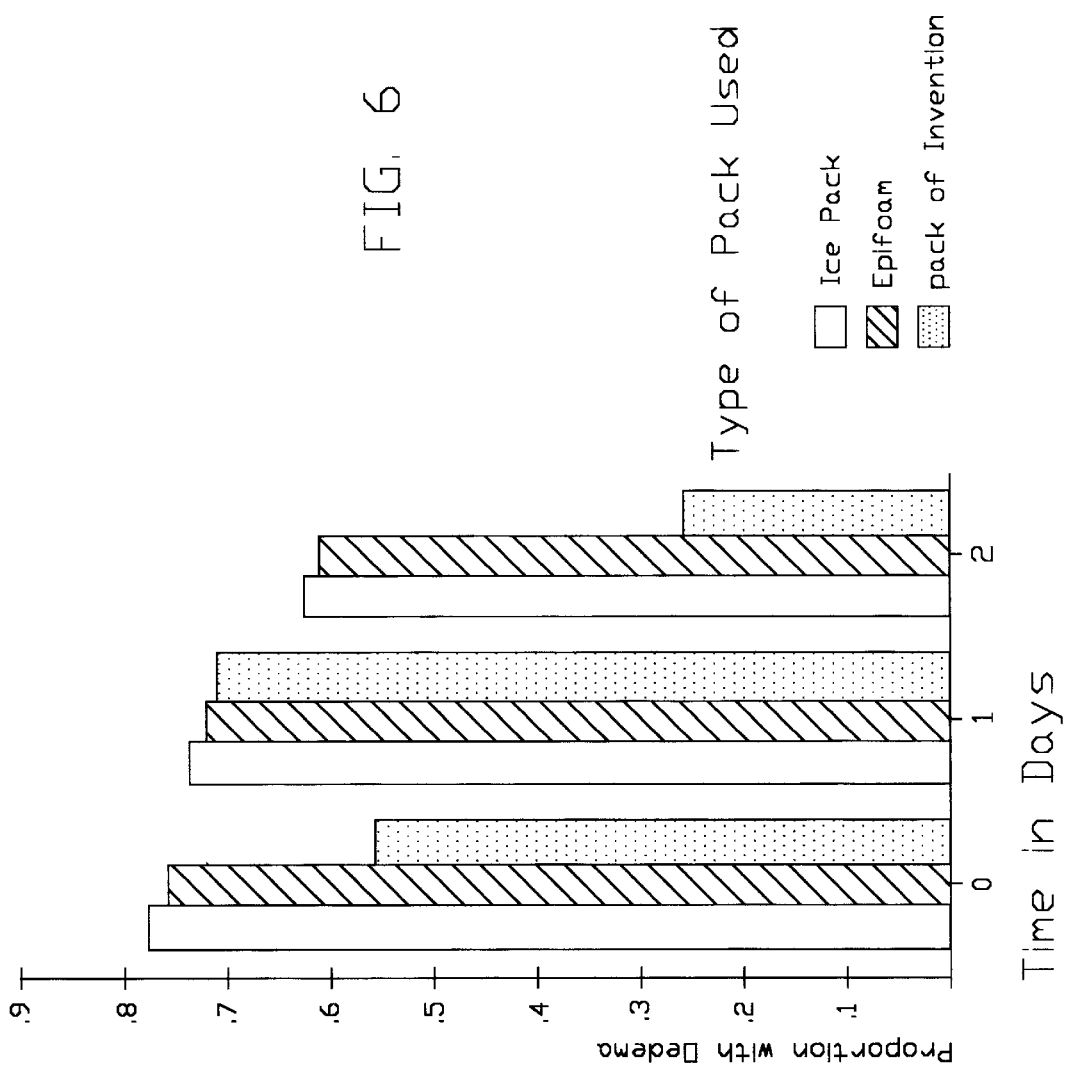
Figure 7:
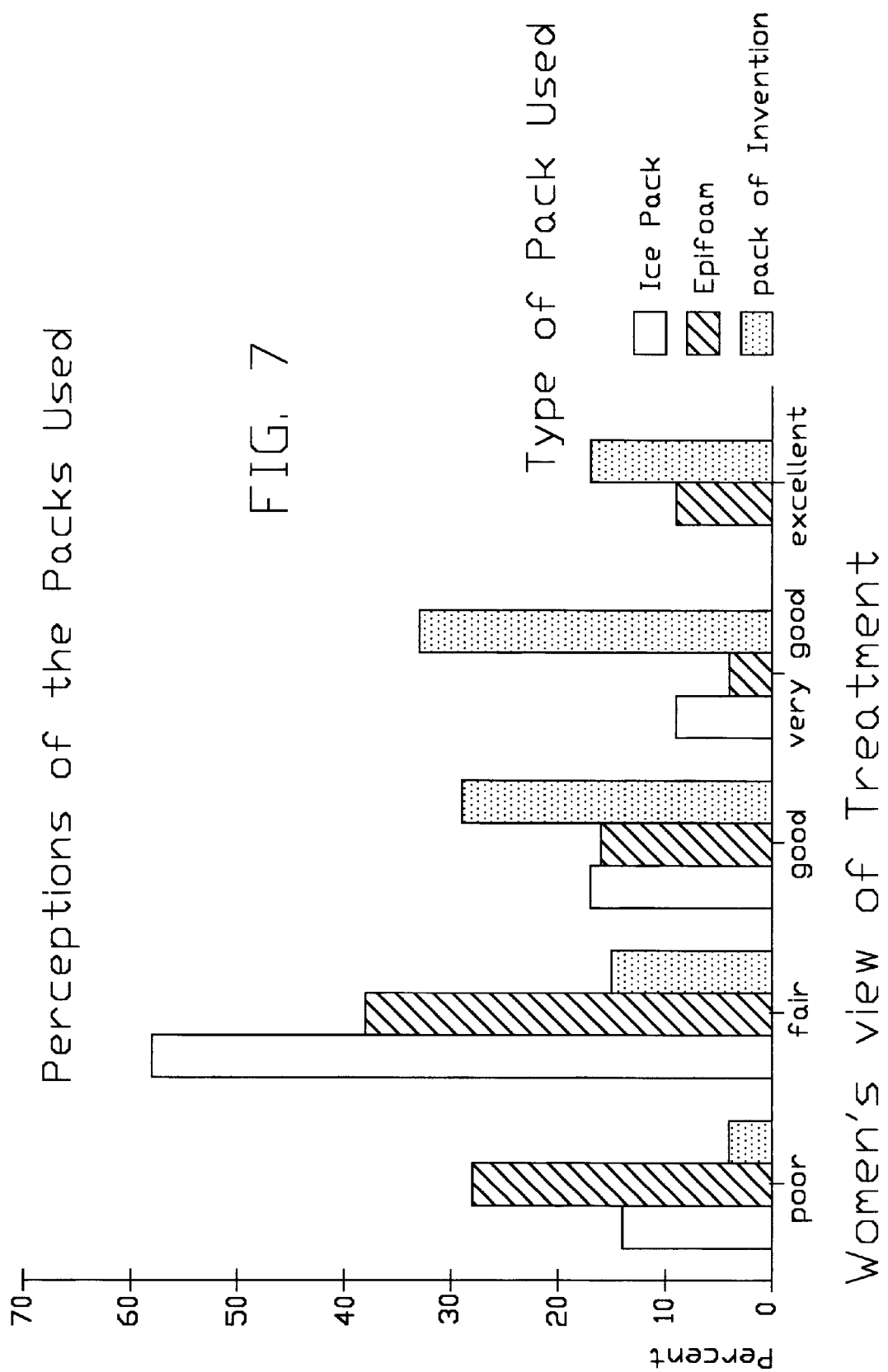

Recently, the applicant has demonstrated the effectiveness of the newly designed device in a randomised controlled clinical trial. The device was compared with the conventional ice pack and epifoam treatments by 120 women following an instrumental birth delivery, who were consulted over a period of 7 months. Perineal oedema/swelling, bruising and self-assessed pain were assessed at regular intervals. The women's opinions were sought as to the benefits of the three treatments at five and ten days post-delivery with a 75% response rate. The results showed no significant change in the level of oedema on Day 1, however, by Day 2, only 26% of women using the device according to the invention indicated oedema when compared with the other two groups which were over 60%. This was statistically significant (P<0.05) See FIG. 6. The majority of women using either ice packs or Epifoam reported the effect of using the same to be fair while the majority of women using the device according to the invention reported the effect to be very good. This was highly statistically significant (P<0.001) See FIG. 7. The women reported that the device was cooling and comfortable to apply, soft and flexible and therefore, mouldable around the perineal/rectal area. 20% of the women also reported that it helped to ease painful haemorrhoids.

In a further feature of the invention the device is of advantage in the treatment of open wounds on any part of the body by providing a cooling and occluding effect thereon and thus it should be appreciated that the invention as herein set out is applicable and of advantage in reducing the trauma of open wounds in tissue and the surrounding area located on any part of the body and reference in the description to the specific effect on perineal and/or rectal trauma should not be interpreted as having a limiting effect on the scope, utility and effectiveness of the device and the protection therein sought for the same and method of use of the same.

What is claimed is:

1. A device for the relief of perineal and/or rectal trauma, said device being reusable a plurality of times comprising an elongate flexible housing within which is sealed a fluid or non-toxic water-soluble gel material comprising 5–7% gelling agent, 30–40% anti-freezing agent, and optionally up to 0.2% antibiotic and up to 0.01% colourant, the remainder being made up of a liquid which has a high thermal capacity so that it is non-freezing the flexible housing and the fluid or gel material remaining pliable at temperatures at least as low as 0 degrees Celsius; and wherein said device is configured for direct application to the perineal and/or rectal area in a cooled condition to provide an initial first stage of a cooling effect on the affected area, and/or an occluding effect on an open wound and a cushioning erect on the affected area and then, after said device has warmed to the temperature of the area to which it is applied, a second stage of at least a cushioning effect, said device being configured and flexible so that it can be used in conjunction with a sanitary towel.

2. A device according to claim 1 wherein the material in the housing is a gel which, even when cooled to below freezing point to −10 degrees Celsius remains in a fluid, pliable state.

3. A device according to claim 1 wherein the gelling agent is hydroxy ethyl cellulose.

4. A device according to claim 1 wherein the anti-freezing agent is propylene glycol.

5. A device according to claim 1 wherein, when included, the antibiotic agent is sodium Nipsept.

6. A device according to claim 1 wherein the gel composition is 5–6% hydroxy ethyl cellulose, 35% propylene glycol, 0–12% sodium Nipsept, 0.001% colourant, the remainder being water.

7. A device according to claim 1, wherein the elongate form of the device has rounded ends.

8. A device according to claim 7 wherein the device is approximately 1–2 cm thick and between 3–4 cm in width and 20–25 cm in length.

9. A device according to claim 1 wherein the device is further provided with adhesive wing portions intermediate the elongate lengthwise edges of the device to allow said device to be attached to items of underwear or the body surrounding the affected area to hold the device in the required position.

10. A device according to claim 1 wherein in use, said device is applied in a cooled condition and heats up gradually thereafter but does not heat up to above the temperature of the area to which it is applied thereby preventing overheating of that area by the device.

11. A device comprising a housing in which is sealed a fluid or non-toxic water-soluble gel material comprising 5–7% gelling agent, 30–40% anti-freezing agent, and optionally up to 0.2% antibiotic and up to 0.01% colourant, the remainder being made up of a liquid which has high thermal capacity so that it is non-freezing, the flexible housing and the fluid or gel material remaining pliable at temperatures at least as low as 0 degrees Celsius; when cooled said device being suitable for application to an open wound on a person to provide a cooling and occluding effect on said open wound and surrounding area.

12. A device according to claim 11 wherein said device also has the added effect of cushioning the open wound and applying pressure to the area surrounding said wound.

13. A method of treating a person for the relief of perineal and/or rectal trauma comprising applying a device to the affected area, said device comprising a flexible housing, said housing being configured for application to the perineal/rectal area and containing a fluid or non-toxic water-soluble gel material comprising 5–7% gelling agent 30–40% anti-freezing agent, and optionally up to 0.2% antibiotic and up to 0.01% colourant, the remainder being made up of a liquid sealed within said housing, said fluid or gel having a high thermal capacity so that it is non-freezing, the flexible housing and fluid or gel material remaining pliable at temperatures at least as low as 0 degrees Celsius, wherein when said device is cooled and then directly applied to the perineal and/or rectal area it conforms to the area to provide an initial first stage of a cooling effect on the affected area, and/or an occluding effect on the open wound and a cushioning effect on the affected area and then after said device has warmed to the temperature of the area to which it is applied, a second stage of at least a cushioning effect.

14. A method according to claim 13 wherein the material in the housing is a gel which, even when cooled to below freezing point to −10 degrees Celsius remains in a fluid, pliable state.

15. A method according to claim 13, wherein the gel has the following composition: 5–6% gelling agent, 35% anti-freezing agent, 0.12% of antibiotic, 0.001% of colourant, and the remainder being made up of water.

16. A method according to claim 15 wherein the gelling agent is hydroxy ethyl cellulose, the anti-freezing agent is propylene glycol and the antibiotic is sodium Nipsept.

17. A method according to claim 13, wherein the device has an elongate form with rounded ends.

18. A method according to claim 13 wherein the device is provided with adhesive wing portions intermediate the elongate lengthwise edges of the device, and the step of applying further includes the step of attaching the wings to items of underwear on the body surrounding the affected area to hold the device in the required position.

19. A method according to claim 13, wherein there is further provided the further step of applying a sanitary towel.

20. A method according to claim 13 wherein in use, said device is applied in a cooled condition and heats up gradually thereafter but does not heat up to above the temperature of the area to which it is applied thereby preventing overheating of that area by the device.

21. A method of treating a person with an open wound by applying a device onto the open wound, said device comprising a flexible housing in which is sealed a fluid or non-toxic water-soluble gel material comprising 5–7% gelling agent, 30–40% anti-freezing agent, and optionally up to 0.2% antibiotic and up to 0.01% colourant, the remainder being made up, of a liquid which has non-freezing characteristics at 0 degrees Celsius so that the flexible housing and fluid or gel material remains pliable at temperatures as low as 0 degrees Celsius to provide a cooling and occluding effect on said open wound and/or cushioning the open wound upon application of pressure to the area surrounding the wound.

22. A device for the relief of perineal and/or rectal trauma, said device comprising a housing of a flexible material within which is sealed a non-toxic water-soluble gel comprising 5–7% gelling agent, 30–40% anti-freezing agent, and, optionally up to 0.2% antibiotic and up to 0.01% colourant, the remainder being made up of a liquid, the gel having a high thermal capacity so that it is non-freezing; the flexible housing and the gel remaining pliable to temperatures at least as low as 0 degrees Celsius; and the device being configured for direct application to the perineal and/or rectal area to provide a cooling effect on the traumatised area and/or an occluding effect on an open wound and/or a cushioning effect on the area.

23. A device according to claim 22 wherein the gel is 5–6% hydroxy ethyl cellulose, 35% propylene glycol, 0.12% sodium Nipsept, 0.001% colourant, and the remainder being water.

24. A method of treating a person for the relief of perineal and/or rectal trauma, comprising the steps of:
    cooling a device comprising a flexible housing within which is sealed a non-toxic, water-soluble gel comprising 5–6% gelling agent, 35% anti-freezing agent, 0.12% antibiotic, 0.001% colourant, the remainder being made up of water; the gel having a high thermal capacity so that it is non-freezing, the device remaining pliable when cooled; and
    applying the device directly to the perineal and/or rectal area to provide a cooling effect on the traumatised area, and/or an occluding effect on an open wound and/or a cushioning effect on the area.

25. A device for the relief of perineal and/or rectal trauma, said device comprising:
    a housing of a flexible material, the housing being configured for direct application to the perineal and/or rectal area; and
    a fluid or gel sealed within the housing, the fluid or gel having a high thermal capacity so that it is non-freezing, the device remaining pliable to temperatures at least as low as 0 degrees Celsius so that it is moldable, in a cooled state, to conform to the perineal and/or rectal area to provide a cooling effect on the traumatised area and/or an occluding effect on an open wound and/or a cushioning effect on the area.

* * * * *